(12) United States Patent
Claus

(10) Patent No.: US 7,277,161 B2
(45) Date of Patent: Oct. 2, 2007

(54) METHOD FOR DISCERNING COLORLESS AND NEAR COLORLESS DIAMONDS AND ARRANGEMENT FOR CARRYING OUT THIS METHOD

(75) Inventor: Patrick Claus, Vinderhoute (BE)

(73) Assignee: Wetenschappelijk en Technisch Onderzoekscentrum Voor Diamant, Lier (BE)

( * ) Notice: Subject to any disclaimer, the term of this patent is extended or adjusted under 35 U.S.C. 154(b) by 379 days.

(21) Appl. No.: 11/074,941

(22) Filed: Mar. 9, 2005

(65) Prior Publication Data

US 2006/0098187 A1    May 11, 2006

(30) Foreign Application Priority Data

Nov. 10, 2004 (BE) ................. 2004/0559

(51) Int. Cl.
  *G01N 21/00* (2006.01)
(52) U.S. Cl. .................................... 356/30
(58) Field of Classification Search ............ None
  See application file for complete search history.

(56) References Cited

U.S. PATENT DOCUMENTS

| 5,164,586 A | * | 11/1992 | Hohberg et al. | ............ 250/226 |
| 5,811,824 A | * | 9/1998 | Smith et al. | ............. 250/559.4 |
| 5,835,200 A |   | 11/1998 | Smith et al. |   |
| 6,650,489 B2 |  | 11/2003 | Ravich et al. |   |

FOREIGN PATENT DOCUMENTS

| DE | 196 10 393 A1 | 9/1997 |
| EP | 0 641 432 B1 | 3/1995 |
| EP | 1 378 748 A1 | 1/2004 |
| FR | 2 528 680 | 12/1983 |
| GB | 2 295 227 A | 5/1996 |
| JP | 57-204440 | 12/1982 |

OTHER PUBLICATIONS

Jean-Pierre Chalain et al., "Detection of GE POL diamonds: a first stage", *Revue de Gemmologie*, No. 138/139, pp. 30-33, Dec. 1999.

* cited by examiner

*Primary Examiner*—Gregory J. Toatley, Jr.
*Assistant Examiner*—Jonathan Skovholt
(74) *Attorney, Agent, or Firm*—Browdy and Neimark, PLLC

(57) ABSTRACT

The invention concerns a method for qualifying a diamond on the basis of a measured light transmission through the diamond, whereby the diamond is radiated by a light source which emits light having a wavelength in a range of 225 nm to 300 nm, whereby the transmission of said light through the diamond is compared to a reference value which corresponds to the transmission of said light through a reference diamond, which is a cut colourless or near colourless diamond with a concentration of A centers between 7 ppm and 22 ppm, and whereby the diamond is classified as natural and not colour-treated if the transmission through the diamond is smaller than or equal to the reference value.

15 Claims, 1 Drawing Sheet

METHOD FOR DISCERNING COLORLESS AND NEAR COLORLESS DIAMONDS AND ARRANGEMENT FOR CARRYING OUT THIS METHOD

BACKGROUND OF THE INVENTION

The invention concerns a method for qualifying a diamond on the basis of a measured light transmission through the diamond, whereby the diamond is irradiated by a light source which emits light having a certain wavelength, and the transmission of this light through the diamond is measured and compared to a reference transmission through a reference diamond.

Ornamental diamonds are in demand for their unique qualities, such as brilliance, fire and scintillation. Natural diamond is so valuable that considerable research is being carried out in order to offer synthetic alternatives. Moreover, more and more treatments are used to increase the market value of low-quality diamonds.

Natural diamonds can be discerned from imitations, synthetic diamonds and treated diamonds on the basis of their physical properties. Laboratories always use several tests on specific characteristics to discern natural diamonds from others.

Diamonds are made up of a lattice of carbon atoms which may be substituted by nitrogen atoms in certain places. The majority of natural diamonds comprise nitrogen in a state of aggregation. They are classified as type Ia. In exceptional cases, nitrogen predominantly occurs as an isolated impurity, what is called type Ib. Rare are natural diamonds having nitrogen concentrations smaller than approximately 30 ppm, called type II. In the case of type Ia, the form of aggregation is usually mentioned as well, i.e. "A" for a substitution in groups of two nitrogen atoms, called A centres, and "B" for a substitution in groups of four nitrogen atoms with a vacancy, called B centres. Type Ia is further divided in IaA, IaB and IaAB as a function of the aggregation forms which can be detected by means of Fourier transformation infrared spectroscopy (FTIR).

The A and B centres hardly contribute to the colour of the diamond in the visible part of the spectrum. However, they provide for a specific absorption in the infrared part of the spectrum, on the basis of which the concentrations can be determined.

Isolated nitrogens, called C centres, strongly contribute to the absorption in the visible part of the spectrum and bring about the typical yellow colour of diamonds.

Natural diamonds usually have a very low content of C centres, i.e. less than 1 ppm, since the nitrogen was able to aggregate all the time these diamonds were situated in the crust of the earth under high pressure and at a high temperature. The temperature however, is limited, namely between 900° C. and 1350° C., so that aggregated nitrogen does not, or hardly split up to isolated nitrogen.

U.S. Pat. No. 6,650,489 describes a viewer for discerning natural, synthetic and treated gem stones. Differences in transmission between various gem stones are visually observed. An adjustable iris must prevent that the user can observe any light which did not go through the gem stone. As the absorption is not standardised to the intensity of the light source, the position of the iris, the size of the stone and other absorbing colour centres, this arrangement is not suitable to accurately discern natural from synthetic or treated diamonds. Moreover, the limit value for the discernment is left to the interpretation of the user and it can only be done in the visible part of the spectrum.

U.S. Pat. No. 6,650,489 also mentions the use of a "phosphorescope" for observing transmission differences in short wave UV. The "SSEF Type II spotter and illuminator" is such an appliance. The diamond to be examined is hereby sealed with clay towards the holder, which is placed above a short wave UV source. A phosphor screen makes it possible to visually observe the transmitted UV light. However, these appliances have numerous disadvantages such as: (i) it is difficult to guarantee the sealing, and it is impossible for the observer to notice this, (ii) the position of being fluorescent of the phosphor screen is to a large degree determined by the cut, such that for some cuts, such as for example the brilliant, only little light will leave the bottom side of the stone if the stone is being illuminated through the table facet, which is the most convenient arrangement in order to avoid leaking light, (iii) the fluorescence of some diamonds will illuminate the screen as well, which may lead to a wrong interpretation, (iv) additional measures must be taken in order to avoid that the observer is exposed to short wave UV, (v) low sensitivity, (vi) the limit value for the discernment is left to the interpretation of the user.

Further, U.S. Pat. No. 5,835,200 describes a method and device to positively identify natural diamonds by detecting what is called the zero phonon line at 415.5 nm, caused by what are called N3 centres, which are typically found in strongly aggregated nitrogen forms, such as in type IaAB diamonds. In order to be able to detect this highly selective absorption, the transmission at about 415.5 nm is scanned in the range of approximately 410 nm to 418.5 nm, by tilting a narrow-band filter. Several registrations including treatment are indicated to detect said narrow absorption peak with sufficient accuracy. The complexity of the arrangement and the wavelength range make this arrangement not suitable to be implemented in a cheap manner, in pocket size and/or fed by means of a battery.

Finally, patent EP 0 641 432 describes a method and appliance to positively identify natural diamonds by means of the registration of the transmission at two different central wavelengths, for example 254 nm and 365 nm. This method comprises the registration of the source intensity at said two wavelengths, and subsequently the registration of the transmission through the diamond at said wavelengths. A diamond is considered to be of the IaA or IaAB type, and consequently as being natural, if the transmission ratio related to the source intensity at 365 nm, namely from 20:1 to 100:1, is considerably larger than that at 254 nm, whereas for type IaB and type II, the ratio is about 2:1 to 1:1.

On the one hand, the transmission ratios related to the source intensity of 20:1 to 100:1 are linked to high concentrations of A centres, larger than 50 ppm, and thus clearly type IaA or IaAB diamonds. As the concentration of A centres is lower, said ratio will be reduced as well. On the other hand, the ratio 1:1 or 2:1 requires very low concentrations of A centres and no colour centres causing any additional absorption towards the deep UV, such as the yellow or brown colour, and thus the most clear crystals. It can be determined, by means of a UV-vis spectrometer, that this ratio may amount to 8:1 in a stone treated by General Electric, marketed under the name GE-POL. Consequently, below 20:1 it is impossible to give a decisive answer about a diamond being either or not natural or HPHT-treated. Measuring at two different wavelengths and the need of reference measurements require wavelength-selective parts and moving parts or a spectrophotometer, which increases the cost price. Consequently, this arrangement is not suitable to be implemented at low cost in pocket size.

SUMMARY OF THE INVENTION

The invention aims to remedy these disadvantages by providing a method which, taking into account the actual commercial diamond synthesises and colour treatments, can classify colourless or almost colourless diamonds as being natural and not colour-treated with great accuracy and discernment, by means of an arrangement which can be made in a technically highly efficient, cheap and compact manner and which can be fed with a small battery.

To this aim, in order to measure the light transmission through a diamond, use is made of a light source which emits light having a wavelength in the range of 225 nm to 300 nm on the one hand, and of a reference diamond which is a cut colourless or almost colourless diamond with a concentration of A centres between 7 ppm and 22 ppm on the other hand, whereby the diamond is classified as being natural and not colour-treated if the transmission through the diamond is smaller than or equal to the transmission through the reference diamond.

Practically, a cut, near colourless diamond with a concentration of A centres of almost 15 ppm is used as a reference diamond, and a light source emitting light having a wavelength of almost 254 nm is used.

In a special embodiment of the invention, a light transmission through a part of the surface of the diamond is measured, and the other part thereof is almost entirely irradiated by the light source which emits the light having said wavelength.

The invention also concerns a device to apply this method, which device mainly comprises the following parts: a detection chamber in which the diamond can be placed, a light source which can emit the light having a certain wavelength in a range of 225 nm to 300 nm in the detection chamber which has an opening through which light can leave the latter, a detector to detect the light intensity of light coming from the detection chamber, a filter which is positioned between the detector and the detection chamber in order to only let through light having certain wavelengths, a processing unit generating a signal as a function of the measured light intensity of the detector, and a user interface representing said signal. This device is characterised in that the opening is smaller than the surface of the flat side of the diamond, such that this side can cover the opening entirely and the light which penetrates the diamond can leave the detection chamber through this opening.

Other particularities and advantages of the invention will become clear from the following description of a few specific embodiments of the method and the device according to the invention; the following description is given as an example only and does not restrict the scope of the claimed protection in any way; the following figures of reference refer to the accompanying drawings.

In both figures, the same reference figures refer to identical or analogous elements.

DETAILED DESCRIPTION OF THE DRAWINGS

The invention in general concerns a device and a method which make it possible to classify colourless diamonds, the so-called colours D to F, and near colourless diamonds, the so-called colours G to J, with great accuracy and discernment, as natural and not colour-treated. The light transmission through the diamond to be examined is hereby determined and compared to a reference transmission of a reference material. The light transmission through the diamond is determined by measuring the light intensity of the light having a certain wavelength which goes through the diamond.

Figure 1:
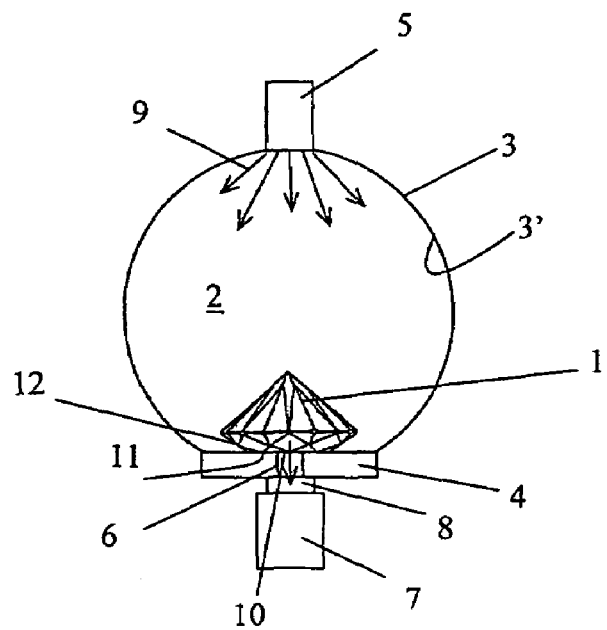
FIG. 1 is a schematic drawing which illustrates the working of the device according to a first embodiment of the invention.

FIG. 1 illustrates a first embodiment of the method according to the invention and of the device used hereby. A diamond 1 is hereby placed in a detection chamber 2 on a supporting surface 4 between a light source 5 and a light detector 7. The supporting surface 4 may consist of a flat plate.

The distance between the light source 5 and the supporting surface 4 is preferably kept as small as possible, taking into account the dimensions of the largest diamond to be examined.

In order to avoid that the detector 7 receives light 9 from the light source 5 which did not penetrate the diamond 1, a screened optical guide is provided between the detector 7 and the diamond 1, formed of a calibrated opening 6 in the supporting surface 4 and which guides light coming from a part 10 of the diamond 1 towards the detector 7.

According to this first embodiment of the invention, the cut diamond 1 to be examined is placed with one of the facets, preferably the table facet 11, on the calibrated opening 6 in the supporting surface 4, whereby this opening 6 has the function of an optical guide, as mentioned above. The supporting surface 4 is hereby not translucent, as a result of which it has a protective function. The supporting surface 4 on the side of the diamond is preferably reflective, such that the light is efficiently coupled through the crown side 12 as well. The diameter of the opening 6 is selected such that it is entirely covered by the facet 11 of the smallest cut diamond one wishes to identify on the one hand, and such that it is sufficiently large to be able to carry out a reliable measurement on the other hand, such that the measuring signal is less sensitive to possible inclusions or zoning of for example nitrogen, which may be found in the diamond. The diameter of the opening preferably amounts to 1 to 2 mm, such that it is possible to carry out an almost bulk measurement.

The light source 5 preferably has a non-directed homogenous radiation at the height of the area where the diamond 1 is being positioned, such that the coupling of light in the diamond is practically independent of its cut and size.

The detection chamber 2 consists of a housing with walls 3 whose inner side 3' is reflective, such that the effect of a pseudo-integrating sphere is obtained and the measured transmission is practically independent of the size and shape of the diamond 1.

In this manner, the light of the light source 5 shining in the detection chamber 2 is efficiently coupled into the diamond 1 via almost the entire surface of the diamond 1. Only at the height of the part 10 of the surface thereof, via which the optical guide 6 guides the light penetrating the diamond 1 to the detector 7, no light 9 coming from the light source 5 is coupled into the diamond 1.

The light source 5 homogenously emits ultra violet light 9 having one or several wavelengths, selected in the range of 225 nm to 300 nm. Diamond has an absolute absorption at a wavelength of 225 nm and a "cut-off" wavelength at 300 nm, which is caused by the presence of A centres in the diamond.

Between the diamond 1 and the detector 7 is placed a narrow-band pass filter 8 which lets light through having a central wavelength selected in the range of 225 nm to 300 nm. This filter 8 preferably passes a strong emission wavelength from the light source 5. Further, the filter 8 is preferably an interference filter having a band width which is smaller than 10 nm.

Some diamonds produce fluorescence and phosphorescence when being radiated with UV light. The filter 8 obstructs the light caused by the fluorescence and phosphorescence of the diamond, such that the detector signal is caused almost exclusively by ultra violet light which has penetrated the diamond.

If the filter 8 is provided on the window 13 of the housing of the detector 7, it is possible to obtain a very compact arrangement.

In order to obtain great accuracy and discernment, the central wavelength of the filter 8 is not set at specific absorption wavelengths. In particular, wavelengths having a strong absorption, which are typical for diamonds which may be synthetic and/or colour-treated, are avoided. Thus, the following typical absorption wavelengths are preferably avoided:

from 265 nm to 276 mm, at which absorption occurs from 5 to 8 $cm^{-1}$ for synthetically produced diamonds;

248 nm and 240 nm, at which absorption occurs for type IaB diamonds, caused by N10 centres;

245 nm and 236 nm, at which absorption occurs to 5 $cm^{-1}$ for diamonds that are synthetically produced according to the temperature gradient method known as such;

234.8 nm, 235.5 nm and 235.9 nm, at which absorption occurs for type IaB diamonds, caused by N9 centres.

An example of a suitable wavelength is 254 nm, which is the major emission line of a mercury lamp. In a range of ±5 nm, namely from 249 nm to 259 nm, there is no typical absorption wavelength whereby a specific absorption occurs which is typical for a synthetic and/or colour-treated diamond. Moreover, a low-pressure mercury lamp is cheap to implement and, when using cold cathode fluorescent lamps (CCFL), can be miniaturised at low cost.

The device according to the invention is calibrated by means of a reference material, such as a cut colourless or near colourless diamond with concentrations of A centres which are about equal to 15 ppm or a calibre which generates an identical measured transmission value in the arrangement. Consequently, a reference transmission is determined by determining the transmission of the reference material in an analogous manner as for the diamond to be examined.

The reference transmission is stored in a processing unit which is not represented in the drawing. This processing unit is connected to the detector 7 and allows to compare the measured value of the transmission of the diamond to be measured with a reference value, namely the measured value of the stored reference transmission.

If the transmission of the diamond to be examined is smaller than the reference transmission, the diamond will be considered to be "natural and not colour-treated". If the measured transmission value is larger than the reference transmission, the diamond will be considered as "to be further examined", and an additional examination is indicated to determine the identity of the diamond.

Figure 2:
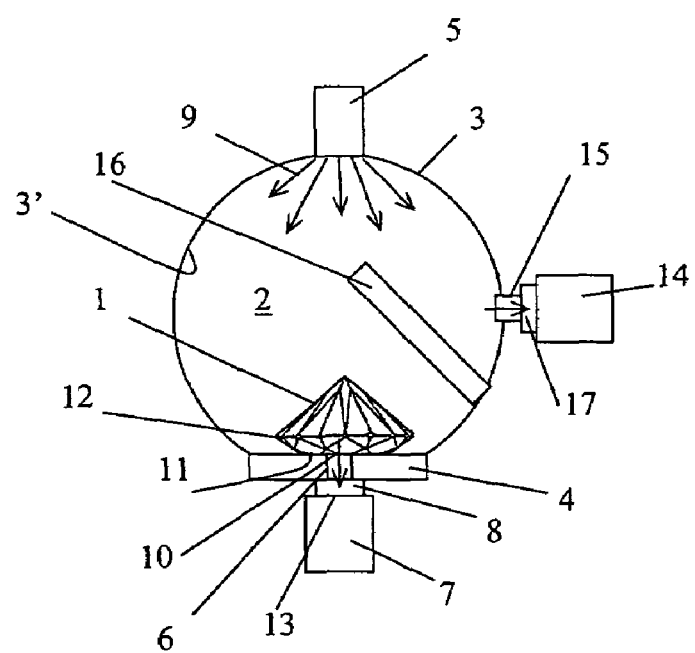
FIG. 2 is a schematic drawing which illustrates the working of the device according to a second embodiment of the invention.

FIG. 2 refers to a second embodiment of the method and device according to the invention which mainly differs from the first embodiment in that the intensity of the light source 5 is also measured via a second detector 14 which receives the light 9 from the light source 5 directly, without said light being coupled to the diamond 1 first. This is advantageous in that the measured transmission is independent from the intensity of the light source. By means of a partition 16, the light path of the light source to the second detector 14 is screened off from the diamond to be examined 1. Opposite the detector 14 is provided, in the same manner as for the detector 7, a screened optical guide which is formed of an inspection opening 15. As is the case with the detector 7 as well, a filter 17 is provided in front of the detector 14, between the latter and the opening 15.

C centres may cause a yellow colour, although there may be other causes. In pure diamonds, a concentration of C centres of about 0.12 ppm results in a colour J. Consequently, colourless or near colourless synthetic or colour-treated diamonds have a concentration of C centres which is smaller than or equal to 0.12 ppm.

Synthetic diamonds predominantly have single nitrogen, i.e. C centres. In the case of high nitrogen contents, such as for type Ib diamonds, the concentration of C centres is larger than 20 ppm, which causes a typical deep yellow colour which is characteristic for the majority of the synthetic diamonds that are used for industrial purposes. In order to produce colourless to near colourless synthetic diamonds, the total nitrogen concentration must be kept low, such as with type II diamonds, since a far advanced aggregation of C centres to A centres, at the synthesis temperature, is not possible on a laboratory time scale. Post-treatments at higher temperatures may accelerate the aggregation of C centres to A centres. However, at temperatures above 1960° C., the A centres split up again, and a thermal equilibrium is created between the A centres and the C centres. Thus, for diamonds with a concentration of A centres of 15 ppm, at the thermal equilibrium at 2300° C., the concentration of C centres will amount to 0.33 ppm, which results in a colour M or N. This colour is outside the scope of the method and device according to the invention for colourless and near colourless diamonds. The length of time during which said equilibrium is reached amounts to about 1 hour, and it is not considered as risk-free for the anvils with HPHT appliances known as such, at 2300° C.

At temperatures below 1960° C., there is no split-up of A centres to C centres and, in principle, it is possible to obtain a far-advanced aggregation like in nature. The migration of simple nitrogen of the C centres in diamonds having a high nitrogen concentration can only be noticed as from 1700° C. on a laboratory time scale. At 1900° C. an aggregation to 80% A centres can be obtained in diamonds having high nitrogen concentration. Practically, synthetic diamonds with a concentration of A centres of about 15 ppm still have a concentration of C centres of some ppm, which is considerably out of the scope of the method and device according to the invention for colourless and near colourless diamonds. Consequently, it is not possible to produce synthetic diamonds according to the present state of the art and to possibly give them a post-treatment in order to obtain a diamond with a concentration of C centres which is smaller than 0.12 ppm and a concentration of A centres which is larger than 15 ppm.

If, in order to obtain a colourless or near colourless diamond, the concentration of C centres in a synthetic diamond is brought to a concentration which is smaller than 0.12 ppm, this will always involve a considerably lower concentration of A centres, such that they will be regarded as "to be further examined" by the method and device of the invention.

Natural diamonds can be treated in HPHT appliances known as such.

As described above, for a diamond with a concentration of A centres of 15 ppm, the concentration of equilibrium for C centres at 2300° C. amounts to 0.33 ppm. Consequently, the treatment of a natural diamond having a concentration of A centres of 15 ppm will always evolve to a colour M or N. If the initial concentration of C centres is higher than the equilibrium, there will be colour improvement. However, the end result stays out of the scope of the method and device according to the invention. If the initial concentration of C centres is lower than the equilibrium, there will be colour deterioration. This is commercially justifiable if it can be compensated by another added value. A recent application of this compensation is the removal of a brown undertone in natural diamonds.

The reason why a diamond has a brown undertone is not known at present, but it is being connected to slip planes in the diamond crystal, and not to the presence of nitrogen. The brown undertone starts to disappear at temperatures equal to some 2100° C. and it can be efficiently removed within 3 to 10 minutes at temperatures of some 2300° C.

For a diamond having an initial concentration of A centres of 15 ppm, after a treatment at 2300° C. of 3 and 10 minutes respectively, the concentration of C centres will amount to 0.04 ppm and 0.12 ppm respectively as a result of the A centres being split up. This can be represented as "A<==>C".

If we assume that the brown undertone masked for example a D colour, this will result in an E colour and a J colour respectively. This is within the colour range of the method and device of the invention. However, when the brown undertone disappears, a considerable amount of vacancies, called V, are released. They are highly mobile and they aggregate with A centres according to the formula "A+V==>H3".

Said H3 centres are colour centres formed of two nitrogens around a vacancy. This creates a deep green to yellow fluorescence, such that the colour of the diamond is turned into a fancy colour. However, the H3 centres are weak and they will be transformed as early as during the treatment, or via a post-treatment, in single nitrogen of the C centres, "H3==>C".

Experiments indicate that the contribution of the vacancies to the transformation via "A+V==>H3==>C" is stronger than the direct split-up via the equilibrium "A<==>C". Thus, in case of a pale brown diamond with a concentration of A centres of 50 ppm, a concentration of C centres of 20 ppm will be produced after 10 minutes of treatment at 2300° C. This concentration of C centres results in a yellow fancy colour. A post-treatment may reduce the concentration of C centres by means of aggregation to A centres. At a concentration of A centres of 15 ppm, it is practically impossible to obtain a concentration of C centres which is lower than 1 ppm, such that these diamonds will be out of the colour range of the method and device according to the invention. As a consequence, we may conclude that no commercial colour improvement is possible for diamonds having a concentration of A centres of more than 15 ppm, for which the result is a colourless or near colourless diamond.

The reference transmission on the basis of which it is decided that the diamond is natural and not colour-treated, is determined with a reference diamond which is a cut diamond having a concentration of A centres which is equal to about 15 ppm. This concentration of A centres can be determined via the specific absorption in the infrared by means of FTIR measurement. Since the measurement is carried out on any cut whatsoever, and not on a plate with a known thickness and light path, we have to take into account an error margin of ±50% when determining an absolute concentration. Consequently, the actual concentration of A centres can be situated between 7 ppm and 22 ppm.

The concentration of equilibrium of C centres, at an initial concentration of A centres of 7 ppm, amounts to 0.22 ppm. This is outside the scope of the method and device according to the invention. The aggregation of C centres to A centres, "C==>A", at an initial concentration of A centres of 7 ppm and temperatures below 1960° C., under practical circumstances leads to concentrations of C centres which are larger than 0.12 ppm. This is outside the scope of the method and device according to the invention. Consequently, it is impossible to produce synthetic colourless or near colourless diamonds with an initial concentration of A centres which is larger than 7 ppm.

After 3 and 10 minutes of treatment at 2300° C., the equilibrium between the concentrations of C centres and A centres, "C<==>A", at an initial concentration of A centres of 7 ppm, will amount to 0.042 ppm and 0.06 ppm respectively. This corresponds to a colour deterioration of about 1 to 2 colour degrees. Vacancies that are created by eliminating a brown undertone still produce, at an initial concentration of A centres of 7 ppm, some ppm C centres which cannot practically be reduced to a value below 0.12 ppm C centres. Consequently, diamonds having an initial concentration of A centres of 7 ppm do not qualify for a commercial colour treatment to colourless or near colourless. Below a concentration of A centres of 7 ppm, the method according to the invention will qualify the diamonds as "to be further examined".

Naturally, the invention is not restricted to the above-described embodiments of the method and device according to the invention as represented in the accompanying drawings.

Thus, for example, in the device according to the invention, the supporting surface which serves as a holder for the diamond and optical guide can be replaced by a separate holder and optical guide. Use can hereby be made of one or several optical fibres which are screened off from the detection chamber and which are provided against a facet of the diamond. The optical guide is screened off from the detection chamber, such that only light can be coupled into the guide which leaves the diamond via the surface of the facet of the latter when it is placed in the detection chamber.

Thus, the transmission can be measured at a certain wavelength by selectively radiating the diamond with light having this wavelength whereby, next, the intensity of said light going through the diamond is measured. Further, the diamond can also be radiated with light having a large spectrum of wavelengths, after which the intensity of the light transmitted by the diamond is measured at certain wavelengths by means of a filter placed in front of the detector.

The detector can also be situated entirely in the detection chamber, and the supporting surface, instead of being a separate plate as represented in the figures, can be part of the inside of the detection chamber. Since no diamond is placed opposite the second detector, as represented in FIG. 2, it goes without saying that no bearing surface must be provided in this place.

The invention claimed is:

1. Method for qualifying a diamond on the basis of a measured light transmission through the diamond, whereby the diamond is radiated by a light source which emits light having a certain wavelength, and the transmission of said light through the diamond is measured and compared to a reference value which corresponds to the transmission of said light through a reference diamond, characterised in that use is made of a light source which emits light having a wavelength in a range of 225 nm to 300 nm, whereby a cut colourless or near colourless diamond with a concentration of A centres between 7 ppm and 22 ppm is selected as said reference diamond, and whereby the diamond is classified as natural and not colour-treated if the transmission through the diamond is smaller than or equal to said reference value, in particular the transmission through the reference diamond.

2. Method according to claim 1, whereby use is made of a cut colourless or near colourless diamond, having a concentration of A centres of almost 15 ppm, as a reference diamond.

3. Method according to claim 1, whereby the light source emits light having a wavelength of 254 nm.

4. Method according to claim 1, whereby the light transmission through a part of the surface of the diamond is measured and the other part of the diamond is radiated almost entirely by the light source which emits light having said wavelength.

5. Method according to claim 1, whereby the diamond is placed in a detection chamber with a flat side on an opening in the detection chamber in such a manner that the opening is entirely covered by the diamond, whereby light from the light source is radiated in the detection chamber, and whereby the intensity of the light from this light source penetrating the diamond and the opening is measured in order to determine the transmission through the diamond.

6. Method according to claim 5, whereby the light from the light source is reflected on the walls of the detection chamber.

7. Method according to claim 1, whereby the light from the light source penetrating the diamond is filtered at a certain wavelength before being measured.

8. Method according to claim 7, whereby the light from the light source penetrating the diamond is filtered at a wavelength in a range of 225 nm to 300 nm.

9. Method according to claim 1, whereby light from the light source is measured which does not penetrate the diamond.

10. Device for qualifying a diamond (1) having at least one flat side (11), optionally for applying the method according to any one of the preceding claims, with a detection chamber (2) in which the diamond (1) can be placed, a light source (5) which can radiate light having a certain wavelength in a range of 225 nm to 300 nm in the detection chamber (2), which has an opening (6, 15) through which light can leave the latter, a detector (7) to detect the light intensity of light coming from the detection chamber (2), a filter (8, 17) which is positioned between the detector (7, 14) and the diamond (1) so as to only let light through having certain wavelengths, a processing unit which contains a reference value and which generates a signal if the light intensity measured by the detector (7) is larger or smaller than the reference value, and a user interface which represents said signal, characterised in that said opening (6) is smaller than the surface of the flat side (11) of the diamond (1), such that this side (11) can cover the opening (6) entirely, and the light which penetrates the diamond (1) can leave the detection chamber (2) via said opening (6), whereby said reference value corresponds to a transmission through a cut colourless or almost colourless diamond with a concentration of A centres between 7 ppm and 22 ppm.

11. Device according to claim 10, whereby the detection chamber (2) has a supporting surface (4) upon which the diamond (1) can be placed and in which said opening (6) is provided.

12. Device according to claim 11, whereby the supporting surface (4) on the side upon which the diamond (1) is placed is reflective.

13. Device according to claim 10, whereby the detection chamber (2) has a reflective inner side (3').

14. Device according to claim 10, whereby the light source (5) is a low-pressure mercury lamp.

15. Device according to claim 10, whereby the detection chamber (2) is a pseudo-integrating sphere in which is situated at least the light source (5).

* * * * *